(12) United States Patent
Doorschodt et al.

(10) Patent No.: US 6,905,871 B1
(45) Date of Patent: Jun. 14, 2005

(54) APPARATUS FOR MECHANICAL PERFUSION OF DONOR'S ORGAN DURING ITS TRANSPORT

(75) Inventors: Benedict Marie Doorschodt, Amsterdam (NL); Joris Emanuel Nicolaas Jaspers, Bodegraven (NL)

(73) Assignee: Universiteit van Amsterdam, Amsterdam (NL)

( * ) Notice: Subject to any disclaimer, the term of this patent is extended or adjusted under 35 U.S.C. 154(b) by 0 days.

(21) Appl. No.: 10/129,870

(22) PCT Filed: Nov. 8, 2000

(86) PCT No.: PCT/NL00/00814

§ 371 (c)(1),
(2), (4) Date: Sep. 18, 2002

(87) PCT Pub. No.: WO01/33959

PCT Pub. Date: May 17, 2001

(30) Foreign Application Priority Data

Nov. 8, 1999 (NL) ............................................. 1013524

(51) Int. Cl.[7] ................................................ A01N 1/00
(52) U.S. Cl. ................................ 435/284.1; 435/286.6; 435/1.2
(58) Field of Search ......................... 435/284.1, 286.5, 435/286.6, 1.2; 128/202.12; 604/41, 43, 44

(56) References Cited

U.S. PATENT DOCUMENTS

| 3,914,954 A | * | 10/1975 | Doerig ..................... 435/284.1 |
| 4,350,477 A | | 9/1982 | Mazal |
| 5,362,622 A | | 11/1994 | O'Dell et al. |
| 5,704,520 A | | 1/1998 | Gross |
| 5,965,433 A | * | 10/1999 | Gardetto et al. .......... 435/284.1 |
| 6,677,150 B2 | * | 1/2004 | Alford et al. ............. 435/284.1 |

\* cited by examiner

*Primary Examiner*—David Redding

(57) ABSTRACT

The invention relates to an apparatus for mechanical organ perfusion during the transport phase of a donor organ, which apparatus comprises an organ receptacle for acommodating the organ, propulsion means for moving the perfusate contained in a liquid compartment of the apparatus to and through the organ receptacle, and oxygenation means for the aeration of the organ receptacle. The propulsion means are embodied as a pump driven by compressed air, while the compressed air serves at the same time for the aeration of the organ receptacle.

10 Claims, 2 Drawing Sheets

FIG. 1

APPARATUS FOR MECHANICAL PERFUSION OF DONOR'S ORGAN DURING ITS TRANSPORT

The invention relates to an apparatus for mechanical organ perfusion during the transport phase of a donor organ, which apparatus comprises an organ receptacle for accommodating the organ, propulsion means for moving the perfusate contained in a liquid compartment of the apparatus to and through the organ receptacle, and oxygenation means for the aeration of the organ receptacle. Such an apparatus is useful, for example, for the transportation of kidneys or livers.

Mechanical organ perfusion during the transport phase of donor organs improves the quality of organs for transplantation. Compared with the known method of cold storage on ice shavings, this method of preservation has important advantages with regard to improving direct graft function, reduction of post-operative dialysis and shortening the stay in hospital. The number of donor organs suitable for transplantation may be greatly increased because mechanical organ perfusion makes it possible to transplant sub-optimal organs. Mechanical organ perfusion further makes it possible to determine the organ's quality and viability prior to transplantation.

In the known organ perfusion system the perfusate is propelled by means of a battery-powered pump and cooled by means of a cooling element and heat exchanger. Oxygenation takes place with the aid of bottled compressed air or oxygen. Because of the size, the weight, and high initial costs and maintenance costs, as well as the necessary operating expertise, the use of the known system is still limited. Only few specialized centres are able to employ this known perfusion system.

It is the object of the invention to provide a simple and inexpensive apparatus for perfusion with which it is possible to achieve a higher success rate of transplantations and to increase the number of usable donor organs.

To this end the apparatus according to the invention is characterized, in that the propulsion means are embodied as a pump driven by compressed air, while the compressed air serves at the same time for the aeration of the organ receptacle. Thus in this system the compressed air required for oxygenation of the perfusate is used for driving the pump, thereby economizing on an electrically-powered pump and battery. This perfusion system is simple and makes perfusion of donor organs possible in all hospitals, thus improving the quality of offered organs. In this way the considerable supply of sub-optimal organs can be made available for transplantation.

A suitable embodiment of the apparatus is thus characterized in that the pump comprises a membrane movably mounted in the liquid compartment, providing a separation between the perfusate contained in the liquid compartment on the one side and the compressed air on the other side, and which membrane assumes a position that depends at least on the pressure of the compressed air directly in communication with the membrane. In this manner a simple movement of the membrane makes it possible to push perfusate present in the liquid compartment into the organ receptacle that is in communication with the liquid compartment, while a reverse movement of the membrane causes the perfusate to be drawn back into the liquid compartment.

This is preferably executed such that the pump comprises a valve which is in communication with the membrane in the liquid compartment and which, subject to the position of the membrane, either allows or blocks the transport of compressed air to the membrane. Depending on the position of the valve, which in turn depends on the position of the membrane, the compressed air thus simply provides the driving force for displacing the perfusate from and to the liquid compartment.

One thing and another is preferably arranged such, that the valve blocks the transport of compressed air to the membrane when and as soon as the membrane reaches a first extreme position at which the volume of the liquid compartment is at a minimum with regard to accommodation of the perfusate, and that the valve subsequently allows the transport of compressed air to the membrane when and as soon as the membrane reaches a second extreme position in which the volume of the liquid compartment is larger than the minimum volume.

In another aspect of the invention the apparatus is characterized in that the valve is provided with a vent to allow a reflux of compressed air to the perfusate when the membrane moves from the second to the first position. The compressed air that primarily served to excite the pump for the transport of the perfusate is thus also used in a simple manner for enriching the perfusate with the necessary oxygen needed for the aeration of the organ receptacle.

A suitable and very simple embodiment in which this may be effectively realized, is characterized in that the liquid compartment is positioned under the organ receptacle, and in that the pump is in communication with the liquid compartment, with the vent of the valve debouching below the perfusate level.

In another aspect of the invention, the apparatus is characterized in that the organ receptacle is provided with a pre-formed, moisture-permeable, relatively soft support for the donor organ. In this way the donor organ to be transported is supported so that shifting and damage, for example, bruises to the organ, may be prevented.

As mentioned earlier, the apparatus according to the invention may be used for the transportation of diverse organs such as kidneys and livers. When the apparatus is intended for the transportation of livers, it is desirable that the liquid compartment be in communication with the organ receptacle via an inlet pipe debouching in a first inlet conduit and a second inlet conduit, which serve for feeding the liver artery and the portal vein of the liver, respectively. The second inlet conduit serving to feed the portal vein needs then preferably to be embodied such that the same transports a substantially continuous stream of perfusate to the portal vein.

In a first embodiment this may be realized simply by the second inlet conduit having an elastic wall such that during use said wall expands due to the pressure in the conduit. This buffs the pulsating action of the perfusate stream. This pulsating action of the apparatus according to the invention imparted on the perfusate stream, actually does have the advantage that it mimics the heart rhythm.

In a second alternative embodiment an expansion vessel may be provided, which is in communication with the second inlet conduit. To both embodiments applies that it is desirable for a non-return valve to be provided in the second inlet conduit near the inlet pipe. This prevents liquid from the second inlet conduit flowing back to the first inlet conduit.

It is further desirable that at least one of the two inlet conduits be provided with an adjustable constriction to allow the proportional adjustment of the perfusate streams in the two inlet conduits.

The invention is also embodied in a pump suitable for use in an apparatus of the kind referred to in the preamble. In accordance with the invention, said pump is characterized in that the same comprises an inlet pipe and an outlet pipe for compressed air, both of which connect to a space which is at least partially defined by a movable membrane, and which comprises valve means providing a mutually excluding connection between the inlet pipe and the space on the one side, and the outlet pipe and the space on the other side. Due to the fact that the valve means either allow a communication between the inlet pipe and the space, or a communication between the outlet pipe and the space, the pump effectively differentiates between an incoming and an outgoing thrust of compressed air.

The valve means are then preferably coupled with the membrane, so that the position of the membrane may determine the position of the valve means.

Thus a convenient and very effective embodiment of the pump is one in which the valve means comprise two parts arranged opposite to one another, a first part of which is provided with a efflux nozzle connected to the inlet pipe, and the second part is provided with a discharge stump connected to the outlet pipe, with the inter-position of a movable valve part between the two parts, capable of non-synchronously closing off the efflux nozzle and the discharge stump.

Preferably there are presser means that effect a position of preference the valve part in which the discharge stump of the second part is closed off, while the efflux nozzle of the first part is open.

As presser means it is possible to use, for example, a spring construction. However, preferably the first part and second part and/or the valve part are made from mutually attracting magnetic materials. This has the advantage of preventing the occurrence of friction as much as possible, so that only very little energy is required to activate the pump.

Thus a desirable embodiment of the pump is characterized in that a catch organ is coupled with the membrane, which catch organ is coupled with the valve part via a coupling sliding over a limited distance in such a manner that when a predetermined distance of displacement is exceeded, the catch organ releases the valve part from the second part until it is in a position where the valve part contacts the first part, and therein closes off the efflux nozzle while the discharge stump is open.

The invention will now be elucidated with reference to the drawings in which

FIG. 1 schematically shows the apparatus according to the invention;

Similar parts in the drawings are referred to by identical reference numbers.

Figure 1:
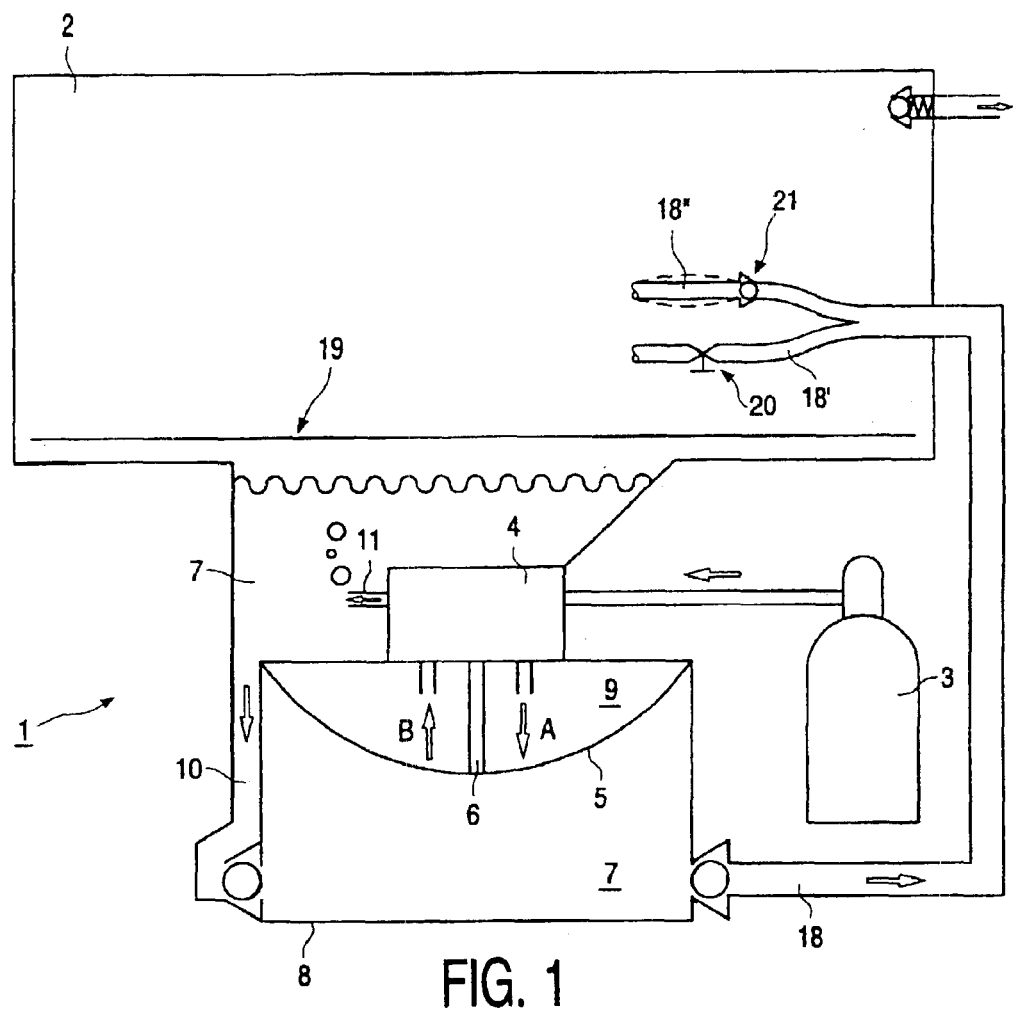

Referring first to FIG. 1, reference number 1 indicates the apparatus for the mechanical perfusion of organs during the transport phase of a donor organ. This apparatus comprises an organ receptacle 2 for accommodating the donor organ and propulsion means 3, 4, 5 for moving perfusate 7 to and through the organ receptacle 2. Further, oxygenation means 3, 4 are provided for the aeration of the organ receptacle 2. The propulsion means 3, 4, 5 are embodied as a pump driven by compressed air from a compressed-air cylinder 3. As will be explained hereinbelow, the compressed air from the compressed-air cylinder 3 additionally serves for the aeration of the organ receptacle 2. The pump 4, 5 is embodied with a membrane 5 movably mounted in the liquid compartment 8, which membrane 5 provides a separation between on the one side the perfusate 7 contained in the liquid compartment 8 and on the other side the compressed air in the space for carrying reference number 9. The membrane assumes a position that depends at least on the pressure of the compressed air in the space 9, that is to say the compressed air directly in communication with the membrane 5. The pump 4, 5 further comprises a valve 4 which is in communication with the membrane 5 mounted in the liquid compartment 8 and which, subject to the position of the membrane 5, either allows or blocks the transport of compressed air 3 from the compressed-air cylinder 3 to the membrane 5. FIG. 1 schematically shows the coupling 6 between the membrane 5 and the valve 4. The valve 4 blocks the transport of compressed air to the membrane 5 when and as soon as the membrane 5 reaches a first extreme position in which the volume of the liquid compartment 8 for the accommodation of the perfusate 7 is at a minimum. The valve 4 then allows the transport of compressed air to the membrane 5 when and as soon as the membrane 5 reaches a second extreme position in which the volume of the liquid compartment 8 is larger than the minimum volume mentioned previously. In this manner the membrane 5 undergoes a reciprocating motion causing the perfusate 7 to be pushed from the liquid compartment 8 into an inlet pipe 18 for the organ receptacle 2, while enabling refluxing perfusate from the organ receptacle 2 to enter the liquid compartment 8 via an outlet pipe 10. To this end the valve 4 is provided with a vent to facilitate the escape of a reflux of compressed air from the space 9 to the perfusate 7 when the membrane moves from the second to the first position, i.e. in the direction indicated by B. FIG. 1 further shows that the liquid compartment 8 is preferably positioned under the organ receptacle 2, and that the pump 4, 5 is located between the liquid compartment 8 and the organ receptacle 2, with the vent 11 of the valve 4 during use debauching below the level of the perfusate 7.

The support 19 for the organ to the transported is indicated very schematically in the Figure. In a particular aspect of the invention it is preferred that said support 19 be comprised of a pre-formed, moisture-permeable, relatively soft material, so that a shift-resistant support is provided for the organ, whereby damage to the organ is prevented.

The apparatus schematically illustrated in FIG. 1 is suitable for the transportation of livers and kidneys as well as other organs. Especially when transporting livers it is desirable for the liquid compartment 8 with the organ receptacle 2 to be in communication via an inlet pipe 18 that opens into a first inlet conduit 18' to feed the liver artery, and a second inlet conduit 18" serving to feed the portal vein of the liver. As the portal vein needs to receive a continuous stream of perfusate rather than a pulsating one, the second inlet conduit 18" may be provided with an elastic wall so that during use said wall expands under the influence of the pulsation pressure in the conduit, thereby buffing the pulsation. This is schematically indicated by a dotted line. Another possibility is to connect an expansion vessel with the second inlet conduit 18". This is not shown but is completely clear to the person skilled in the art. The second inlet conduit 18" is preferably provided near the inlet pipe 18 with a non-return valve 21 to prevent liquid from the second inlet conduit 18" flowing into the first inlet conduit 18'. Finally, the Figure shows that in the first inlet conduit 18', an adjustable constriction 20 is provided to allow the proportional adjustment of the liquid streams in the first inlet conduit 18' and the second inlet conduit 18".

Figure 2:
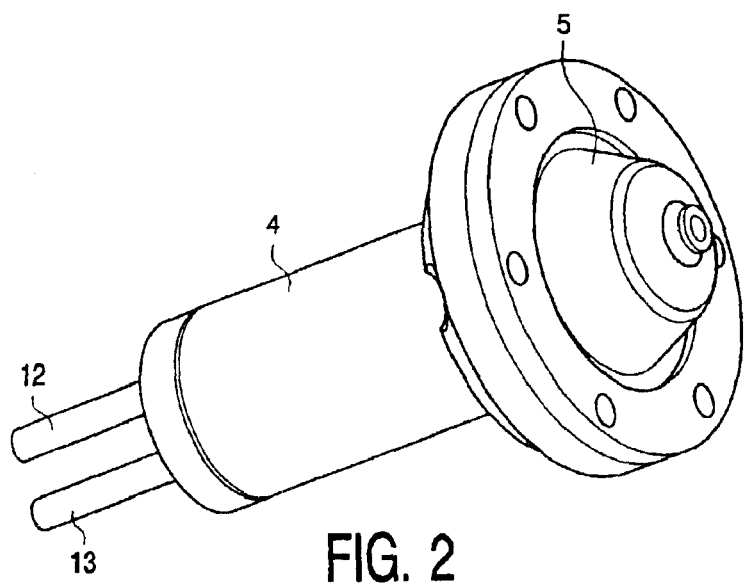
FIG. 2, shows a perspective view of a pump according to the invention.

Referring now to the FIGS. 2 and 3, the pump 4, 5 according to the invention will now be explained in more detail. Said pump 4, 5 is especially suitable for use in an apparatus as described heretofore. In the pump 4, 5 a valve part 4 and a membrane 5 may be distinguished (see FIG. 2). Further provided are an inlet pipe 12 and an outlet pipe 13 for compressed air, both of which are in communication with a space in the interior of the pump 4, 5, which space is at least partially defined by the movable membrane 5. The valve means 4 provide a mutually excludable connection between on the one side the inlet pipe 12 and the space, and on the other side the outlet pipe 13 and the space. The valve means 4 are further physically coupled with the membrane 5 in a manner that will be elucidated below with reference to FIG. 3.

Figure 3:
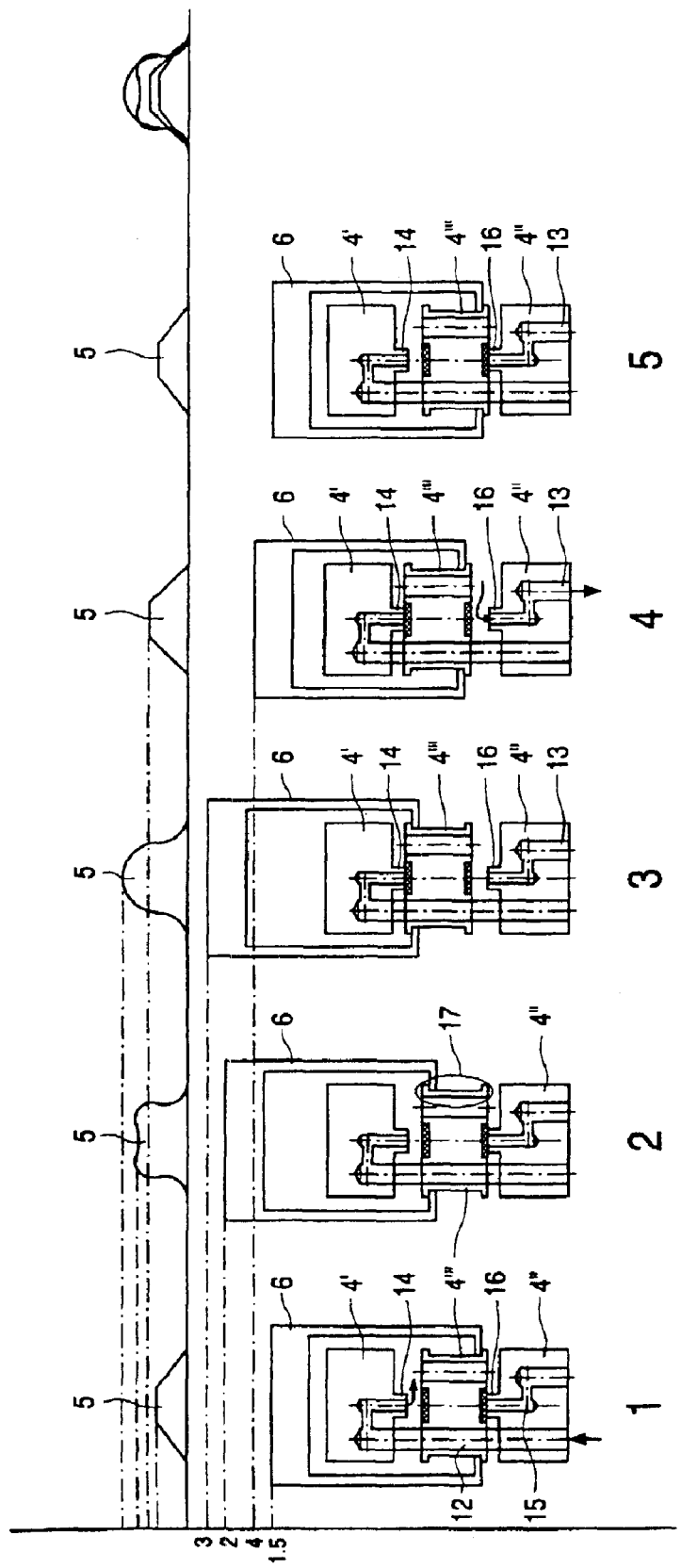
FIG. 3, shows five successive positions of a number of parts that constitute the pump according to the invention.

FIG. 3, very schematically shows a few parts that are part of the pump 4, 5 according to the invention. The successive positions that may be assumed by the parts of the pump 4, 5 are indicated by the numbers 1 to 5, respectively. Referring first to the position indicated by number 1, it is shown that the valve means 4 comprise two parts 4', 4" arranged opposite to one another, a first part 4' of which is provided with an efflux nozzle 14 connected to the inlet pipe 12, and the second part 4" is provided with a discharge stump 16 connected to the outlet pipe 15, with the interposition between the two parts 4', 4" of a movable valve part 4''', which is capable of non-synchronously closing off the efflux nozzle 14 and the discharge stump 16. The position indicated by number 1 illustrates how via the inlet conduit 12 and efflux nozzle 14 compressed air can reach the membrane 5, which subsequently inflates, as shown in the positions indicated by numbers 2 and 3. The valve means 4' and 4" are further provided with presser means that provide a position of preference of the valve part 4''', wherein the discharge stump 16 of the second part 4" is closed off, and the efflux nozzle 14 of the first part 4' is open. For this purpose the first part 4' and second part 4" and/or the valve part 4''' are preferably made from mutually attracting magnetic materials. Thus in the position indicated by number 1, compressed air is prevented from escaping. The inflation of the membrane 5 causes the same to catch a catch organ 6 that is coupled thereto. Said catch organ is coupled with the valve part 4''' via a coupling 17 sliding over a limited distance in such a manner that when a predetermined distance of displacement is exceeded, the catch organ 6 releases the valve part 4''' from the second part 4" until it reaches the position indicated by number 3, where the valve part 4''' contacts the first part 4', and therein closes off the efflux nozzle 14, while the discharge stump 16 is open. In this situation the membrane 5 cannot inflate any further and the reverse happens in that compressed air escapes from the space defined by membrane 5 via the discharge stump 16 which provides the communication with the discharge pipe 13. Due to the 5 elasticity of the membrane or due to a spring construction, the catch organ 6 moves to a position where the valve part 4''' is lifted from the first part 4' and is moved in the direction of the second part 4". In the position indicated by number 5, the final situation is reached where the valve part 4''' is returned onto the second part 4", thereby closing off the discharge stump 16 which provides the communication with the discharge pipe 13, while the efflux nozzle 14 of the first part 4' is open. From this situation the cycle is repeated as explained, departing from the position indicated by number 1. The frequency of the pump according to the invention may be adjusted by regulating the pressure of the compressed air. The pumping rate is also adjusted by this means.

What is claimed is:

1. An apparatus for mechanical organ perfusion during the transport phase of a donor organ, which apparatus comprises an organ receptacle for accommodating the organ, propulsion means for moving the perfusate contained in a liquid compartment of the apparatus to and through the organ receptacle, and oxygenation means for the aeration of the organ receptacle, wherein the propulsion means are embodied as a pump driven by compressed air, while the compressed air serves at the same time for the aeration of the organ receptacle, and wherein the pump comprises a single membrane movably mounted in the liquid compartment and below the organ receptacle, providing a separation between the perfusate contained in the liquid compartment on one side and the compressed air on another side, and which membrane assumes a position that depends at least on pressure of the compressed air directly in communication with the membrane.

2. An apparatus according to claim 1, wherein a valve is in communication with the membrane in the liquid compartment and which, subject to the position of the membrane, either allows or blocks the transport of compressed air to the membrane.

3. An apparatus according to claim 2, wherein the valve blocks the transport of compressed air to the membrane when and as soon as the membrane reaches a first extreme position at which the volume of the liquid compartment is at a minimum with regard to accommodation of the perfusate, and that the valve subsequently allows the transport of compressed air to the membrane when and as soon as the membrane reaches a second extreme position in which the volume of the liquid compartment is larger than the minimum volume.

4. An apparatus according to claim 2 wherein the valve is provided with a vent to allow a reflux of compressed air to the perfusate when the membrane moves from the second to the first position.

5. An apparatus according to claim 1, wherein the organ receptacle is provided with a pre-formed, moisture-permeable, relatively soft support for the donor organ.

6. An apparatus according to claim 1 for the transportation of livers, wherein the liquid compartment is in communication with the organ receptacle via an inlet pipe debauching In a first inlet conduit and a second inlet conduit, which serve for feeding the liver artery and the portal vein of the liver, respectively.

7. An apparatus according to claim 6, wherein the second inlet conduit has an elastic wall such that during use said wall expands due to the pressure in the conduit.

8. An apparatus according to claim 6, wherein an expansion vessel is coupled with the second inlet conduit.

9. An apparatus according to claim 6, wherein a non-return valve is provided in the second inlet conduit near the inlet pipe.

10. An apparatus according to claim 6, wherein at least one of the two conduits is provided with an adjustable constriction.

* * * * *